United States Patent
Patel

(10) Patent No.: US 10,342,769 B2
(45) Date of Patent: Jul. 9, 2019

(54) CARMUSTINE PHARMACEUTICAL COMPOSITION

(71) Applicant: Mahendra R. Patel, Milltown, NJ (US)

(72) Inventor: Mahendra R. Patel, Milltown, NJ (US)

(73) Assignee: Navinta III Inc, Boca Raton, FL (US)

( * ) Notice: Subject to any disclaimer, the term of this patent is extended or adjusted under 35 U.S.C. 154(b) by 0 days.

(21) Appl. No.: 14/936,227

(22) Filed: Nov. 9, 2015

(65) Prior Publication Data

US 2016/0136116 A1 May 19, 2016

Related U.S. Application Data

(60) Provisional application No. 62/080,091, filed on Nov. 14, 2014.

(51) Int. Cl.

| | | |
|---|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A61K 31/175* | (2006.01) |
| *A61K 9/19* | (2006.01) |
| *A61K 31/00* | (2006.01) |
| *A61K 47/10* | (2017.01) |

(52) U.S. Cl.
CPC .............. *A61K 31/175* (2013.01); *A61K 9/19* (2013.01); *A61K 31/00* (2013.01); *A61K 47/10* (2013.01)

(58) Field of Classification Search
None
See application file for complete search history.

(56) References Cited

U.S. PATENT DOCUMENTS

| | | |
|---|---|---|
| 4,659,699 A | 4/1987 | Francis |
| 5,066,647 A | 11/1991 | Palepu et al. |
| 5,130,305 A | 7/1992 | Palepu et al. |
| 5,227,373 A | 7/1993 | Alexander et al. |
| 5,227,374 A | 7/1993 | Alexander et al. |
| 5,268,368 A | 12/1993 | Palepu |
| 5,413,995 A | 5/1995 | Alexander et al. |
| 5,418,223 A | 5/1995 | Palepu et al. |
| 5,770,230 A | 6/1998 | Teagarden et al. |
| 5,972,912 A | 10/1999 | Marek et al. |
| 6,613,927 B1 | 9/2003 | Kwok |
| 8,436,190 B2 | 5/2013 | Brittain et al. |
| 8,609,863 B2 | 12/2013 | Brittain et al. |
| 2002/0051749 A1 | 5/2002 | Faisant et al. |
| 2005/0020615 A1 | 1/2005 | Rubino |
| 2006/0159713 A1 * | 7/2006 | Brittain ................ A61K 9/0019 424/400 |
| 2009/0264488 A1 | 10/2009 | Cooper et al. |
| 2012/0071532 A1 | 3/2012 | Cooper et al. |
| 2013/0041003 A1 | 2/2013 | Brittain et al. |
| 2013/0123316 A1 | 5/2013 | Brittain et al. |

FOREIGN PATENT DOCUMENTS

WO 2008119260 A1 10/2008

OTHER PUBLICATIONS

Flamberg et. al, Low temperature vacuum drying of sterile parenterals from ethanol, Bulletin of Parenteral Drug Association, Sep.-Oct. 1970, vol. 24(5), pp. 209-217.

Ni et. al,, Use of pure t-butanol as a solvent for freeze-drying: a case study, 2001, International Journal of Pharmaceutics, vol. 2001, pp. 39-46.

* cited by examiner

*Primary Examiner* — Layla Soroush

(74) *Attorney, Agent, or Firm* — St. Onge Steward Johnston & Reens LLC

(57) ABSTRACT

The present invention provides pharmaceutical formulations of lyophilized carmustine suitable for pharmaceutical use. The present invention further provides methods of producing lyophilized carmustine. The pharmaceutical formulations can be used for any disease that is sensitive to treatment with carmustine, such as neoplastic diseases.

8 Claims, No Drawings

CARMUSTINE PHARMACEUTICAL COMPOSITION

FIELD OF THE INVENTION

The present invention relates to pharmaceutical compositions for the treatment of various diseases, such as neoplastic diseases and autoimmune diseases. In particular, it relates to pharmaceutical formulations comprising a nitrogen mustard, such as carmustine.

BACKGROUND OF THE INVENTION

Nitrogen mustards are cytotoxic chemotherapy agents for the treatment of various diseases, such as neoplastic diseases and autoimmune diseases. Because of their high reactivity in an aqueous solution, nitrogen mustards are difficult to formulate as pharmaceuticals and are often supplied for administration in a lyophilized form that requires reconstitution by skilled hospital personnel prior to administration. Nitrogen mustards are prone to degradation in an aqueous solution. Thus, after reconstitution, the product should be promptly administered to a patient, Carmustine is one species of nitrogen mustards. Specifically, it is a β-chloro-nitrosourea compound useful in chemotherapy of certain neoplastic diseases. Carmustine has the chemical name: 1,3-bis (2-chloroethyl)-1-nitrosourea, with a molecular weight of 214.06 and the following structure (Formula I):

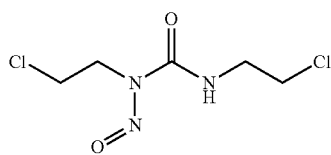

Formula I

Carmustine is also called a dialkylating agent because it may provide two alkylating groups. It is very soluble in alcohol, such as tertiary butanol (also known as 2-methyl-propan-2-ol, tert-butanol, t-butanol, t-butyl alcohol, or TBA), dichloromethane, and ether, and slightly soluble in water with a solubility of 4 mg/mL. Carmustine readily gets hydrolyzed in water at pH>6. Carmustine has a Log P value of 1.53. Its antineoplastic activity is mainly due to its effect on DNA, RNA, mitochondrial glutathion reductase and Cytochrome P450 enzyme.

Carmustine is commercially available as a sterile lyophilized powder for injection under the tradename BiCNU®. BiCNU® (carmustine for injection) is indicated for brain tumors, multiple myeloma, Hodgkin's disease, and non-Hodgkin lymphoma (NHL). The lyophilized dosage formulation of carmustine typically contains no preservatives and is not intended for use as a multiple dose vial. BiCNU® (carmustine for injection) is available in single dose vials containing 100 mg of lyophilized powders of carmustine in each vial. Sterile diluent for constitution of BiCNU® (carmustine for injection) is co-packaged with the active drug product (i.e., lyophilized carmustine) for use in constitution of the lyophilsate. The lyophilized carmustine appears as pale yellow dry flakes or dry congealed mass. Prior to injection, the lyophilized carmustine is reconstituted with a diluent with ethanol and the solution is further diluted with water. The reconstitution results in a clear, colorless to yellowish solution which may be further diluted with 5% Dextrose Injection, USP.

Camustine has a low melting point of 30.5° C. to 32.0° C., exposure of carmustine to this temperature or above will cause the drug to liquefy and appear as an oil film on the vials. This may be a sign of decomposition and vials may need to be discarded. For this reason, carmustine is it is typically stored at 2-8° C. in a sealed vial. Unopened BiCNU® vials may provide a stable product for up to 3 years. After reconstitution, BiCNU® is stable for 24 hours under refrigeration at 2-8° C. Reconstituted vials should be examined for crystal formation prior to use. If crystals are observed, they may be redissolved by warming the vial to room temperature with agitation.

The preparations of carmustine, its pharmaceutically acceptable salts, and/or compositions thereof, have been disclosed in the prior art. For example, Flamberg et al. discloses a low temperature vacuum drying process for preparing sterile carmustine from an ethanol solution, in which ethanol is the only solvent. (Flamberg et al., Low temperature vacuum drying of sterile parenterals from ethanol, *Bulletin of Parenteral Drug Assoc.* 1970 Sep.-Oct. 24 (5):209-17). The nature of the product described in this publication is very similar to what is currently on the market as a commercial product, BiCNU®.

One issue in the manufacturing process of the commercial product BiCNU® is that lyophilized carmustine deposited in a glass container tends to reach up to the neck of a glass container. As a result, there is a risk for drug exposure to operators, potential loss of product, and potential loss of potency in the lyophilization chamber. The commercial product BiCNU® may also show undesirable signs of particulate matter, signs of melting or liquidification present in the product.

There is a need for an improved, robust carmustine formulating process. There is also a need for a lyophilized formulation of carmustine which produces better quality powder cakes, improved stabilities, and improved impurity profiles than the lyophilized powder of carmustine currently on the market.

SUMMARY OF THE INVENTION

The present invention is directed to a stable pharmaceutical composition of carmustine suitable for lyophilization and a lyophilized carmustine formulation which is useful in the treatment of various neoplastic diseases.

In one aspect, the present invention provides a novel pharmaceutical composition comprising carmustine in t-butanol. In some embodiments of the pharmaceutical composition, t-butanol is present at a concentration of about 5% (v/v) to about 100% (v/v). The pharmaceutical composition may contain carmustine at a concentration of about 3 to about 400 mg/mL, preferably about 10 to about 200 mg/mL, more preferably about 25 to about 150 mg/mL, and even more preferably about 50 to about 100 mg/mL.

The pharmaceutical composition may further comprise one or more other alcohols. Suitable alcohols include, but are not limited to, methanol, ethanol, n-propanol, isopropanol, and n-butanol.

In another aspect, the present invention provides a novel pharmaceutical composition comprising carmustine in an alcohol, wherein the alcohol is selected from the group consisting of methanol, ethanol, n-propanol, isopropanol, n-butanol, and mixture thereof.

The carmustine pharmaceutical composition in an alcoholic solution is particularly suitable for lyophilization to generate lyophilized carmustine with an improved impurity and stability profile. In this context, the pharmaceutical composition is a pre-lyophilization composition. According to some embodiments, the carmustine composition contains not more than about 0.3%, more preferably not more than about 0.2%, even more preferably not more than about 0.1% of 1,3-bis(2-chloroethyl)urea, a degradation product of carmustine, at time zero after preparation.

1,3-bis(2-chloroethyl)urea is referred as carmustine related substance A ("RS A") in this application. It has the following chemical structure as shown in Formula II:

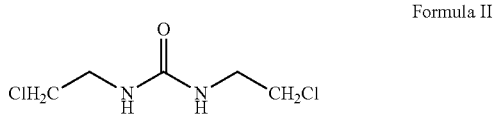

Formula II

In a further aspect, the present invention provides a method for preparing a pharmaceutical solution of carmustine for lyophilization. The present invention additionally provides a novel lyophilization process for manufacturing a lyophilized pharmaceutical composition that controls the level of carmustine degradation impurities. The total carmustine impurities in the final product are less than about 1.0% of total known and unknown impurities.

The lyophilization process comprises the steps of: dissolving carmustine in an alcohol or alcohol blend, freezing the carmustine solution, removal of the alcohol or alcohol blend by freeze-drying at a first freeze-drying temperature, and optionally a secondary freeze-drying at a temperature above the first freeze-drying temperature, to obtain the lyophilized pharmaceutical composition, wherein the alcohol or alcohol blend comprises t-butanol. The resulting lyophilized carmustine may have an improved cake appearance.

The alcohol blend used in the lyophilization process may be a mixture of t-butanol and another alcohol selected from the group consisting of methanol, ethanol, n-propanol, isopropanol, and n-butanol.

In yet another aspect, the present invention provides a method of treating a patient in need, which comprises the steps of: reconstituting the lyophilized carmustine composition into an aqueous solution, optionally followed by diluting the resulting solution, and administering an effective amount of the aqueous carmustine solution to a mammal in need thereof. The patient in need may suffer from brain tumors, multiple myeloma, Hodgkin's disease, and non-Hodgkin lymphoma (NHL).

DETAILED DESCRIPTION OF THE INVENTION

The invention provides stable, pharmaceutically acceptable compositions of carmustine. In particular, the invention provides formulations for the lyophilization of carmustine. The lyophilized powder obtained from such formulations is more easily reconstituted than the presently available lyophilized powder of carmustine. Further, the lyophilized products of the present invention have a better impurity profile than BiCNU® with respect to certain impurities, in particular 1,3-bis(2-chloroethyl)urea (RS A) prior to reconstitution, upon storage of the lyophilized products, or following reconstitution. The present invention further provides formulations of carmustine useful for treating neoplastic diseases. The formulations described herein can be administered alone or in combination with additional antineoplastic agent and/or radioactive therapy.

As described herein, a lyophilized formulation of carmustine is obtained by removal of organic solvent(s) in a carmustine pharmaceutical composition for lyophilization (i.e., pre-lyophilization composition). The pharmaceutical composition for lyophilization comprises carmustine dissolved in organic solvent(s). It is preferred to choose an organic solvent in which carmustine has a high solubility so that a concentrated carmustine solution may be obtained. It is also preferred that the solvent may be easily removed from a carmustine solution through, for example, lyophilization or vacuum drying. The solution contains carmustine at a concentration of about 3 to about 400 mg/mL, preferably about 10 to about 200 mg/mL, more preferably about 25 to about 150 mg/mL, and even more preferably about 50 to about 100 mg/mL.

The term "lyophilization" (also known as freeze-drying, lyophilisation, or cryodesiccation) means a process of removal water or other solvents by freezing a material containing water and/or other solvents followed by reducing the surrounding pressure to allow the frozen water and/or other solvents in the material to sublimate directly from the solid phase to the gas phase.

One of the most suitable solvent systems for preparing the pre-lyophilization pharmaceutical composition is tert-butanol: and dehydrated alcohol in a ratio of 100:0 (v/v) to 5:95 (v/v), preferably 90:10 (v/v), wherein the dehydrated alcohol is an alcohol other than tert-butanol. Dehydrated alcohol means anhydrous alcohol. The pharmaceutical grade anhydrous ethanol may also be referred as dehydrated ethanol. tert-Butanol used in the present invention is preferably anhydrous. In other words, the tert-butanol is 100 v/v % when tert-butanol: a dehydrated alcohol in a volume ratio of 100:0; and the tert-butanol is 95 v/v % when tert-butanol: a dehydrated alcohol in a volume ratio of 95:5. The term "v/v %" means the volume of a solute in the total volume of solution. As one skilled in the art would understand, when the solute is a liquid sometimes, it is convenient to express its concentration in volume/volume percent (v/v %). The calculation of v/v % is:

$$\text{Concentration solute}(v/v\%) = \frac{\text{volume solute (mL)}}{\text{Total volume of solution (mL)}} \times 100$$

Other solvents may be used in the pre-lyophilization pharmaceutical composition. Suitable solvents are those in which carmustine is relatively stable and will not appreciably degrade or deactivate the active pharmaceutical ingredient (i.e., "API", and in this case, carmustine). Such solvents may include ethanol, n-propanol, n-butanol, isopropanol, ethyl acetate, dimethyl carbonate, acetonitrile dichloromethane, methyl ethyl ketone, methyl isobutyl ketone, acetone, 1-pentanol, methyl acetate, methanol, carbon tetrachloride, dimethyl sulphoxide, hexafluoroacetone, chlorobutanol, dimethyl sulphone, acetic acid, and cyclohexane. The above solvents may be used individually or in combination.

One or more pharmaceutically acceptable excipients can be present in the pre-lyophilization solution. Examples of excipients that may be used in the present invention include, without limitation, sodium or potassium phosphate, citric acid, tartaric acid, gelatin, glycine, and carbohydrates such as lactose, sucrose, maltose, mannitol, glycerin, dextrose, dextran, trehalose and hetastarch. Other excipients that may be used include antioxidants, such as, without limitation, ascorbic acid, acetylcysteine, cysteine, thioglycerol sodium hydrogen sulfite, butyl-hydroxyanisole, butyl-hydroxytoluene, alpha-tocopherol acetate, and chelators.

Lyophilization may be carried out using a standard equipment for lyophilization or vacuum drying. A lyophilization cycle may vary depending upon the equipment and facility used.

In general, an alcoholic pre-lyophilization solution or dispersion is first formulated in a pharmaceutically acceptable compounding vessel. The solution is aseptically filtered into a sterile container, filled in to vials, partially stoppered, and loaded into a lyophilizer (i.e., lyophilization equipment). The solvent or solvent blend is lyophilized until a moisture content in the vials reaches about 0.1 to about 8.0%. The resulting lyophilized powder (i.e., lyophilsate) is stable at about 2° C. to about 8° C. for up to 3 years. The lyophilsate may be readily reconstituted with a diluent or other suitable carrier to provide a liquid formulation of carmustine suitable for administration (e.g., by parenteral injection).

The pre-lyophilization solution or dispersion may be formulated by: 1) dissolving/dispersing carmustine in an alcohol (for example, about 10% of the final total volume), preferably a dehydrated alcohol, at an ambient temperature, 2) adding a co-solvent, preferably an alcohol, most preferably TBA, at room temperature, preferably at about 25° C., to achieve the final volume, and mixed well, and 3) cooling the solution to about 1° C. to about 8° C., preferably about 5° C. Although the preceding steps are described in a certain order, one skilled in the art will understand that he may change the order of the steps and quantities of each component as needed.

The pre-lyophilization solution may be sterilized prior to lyophilization. Sterilization may be performed by aseptic filtration, e.g. through a 0.22μ filter. Multiple sterilization filters may also be used.

After sterilization, the solution is ready for lyophilization. The filtered solution will be introduced into a sterile receiving vessel, and then transferred to any suitable containers in which the formulation will be lyophilized. The formulation may also be lyophilized in the containers in which the product will eventually be sold and packed, for example, in vials.

A typical procedure for use in lyophilizing the pre-lyophilization solution is set forth below. However, a person skilled in the art would understand that modifications to the procedure or process may be made depending on factors such as pre-lyophilization solution, lyophilization equipment, and lyophilization parameters.

Initially, the pre-lyophilization solution is placed in a lyophilization chamber and cooled to a temperature well below the freezing point of the pre-lyophilization solution for several hours. Preferably, the temperature is at or below about −60° C. and held for at least 2 hours. After the pre-lyophilization solution is frozen completely, the chamber and the condenser are evacuated with vacuum pumps. The condenser surface has been previously chilled by a circulating refrigerant prior to the vacuum evacuation. Preferably, the condenser has been chilled below the freezing point of the solvent(s) preferably to about −40° C., more preferably to about −50° C. or lower, even more preferably to about −60° C. or lower. Additionally, evacuation of the chamber continues until a pressure of about 75 to about 1600 mT, preferably about 75 to about 900 mT, even more preferably about 100 to about 500 mT, is reached.

The frozen product (i.e., frozen pre-lyophilization composition) is then warmed under vacuum in the chamber and condenser. Usually this is carried out by warming the shelves within the lyophilizer on which the frozen product rests during the lyophilization process. The warming process optimally takes place very gradually, over a course of several hours. For example, the product temperature may initially be increased from about −50° C. to about 10° C. and maintained for a period from about 5 to about 70 hours. Additionally, if required, the product temperature may further be increased from the freezing temperature to about 10° C. to about 40° C. over a period of about 1 to about 100 hours. To prevent disruption of the lyophilized cake and loss of the product from the vials that contain the product, complete removal of the organic solvent(s) is preferably performed during the initial drying phase. Complete drying may be indicated when the vacuum, condenser temperature, and product shelf temperature are stabilized. After the initial drying, the product temperature may be increased to about 10° C. to about 40° C. and maintained for a period from about 5 to about 40 hours.

Once the drying cycle is complete, the chamber pressure can be slowly increased to an atmospheric pressure (or slightly below) by introducing a sterile, dry nitrogen gas or other inert gas. If the product composition has been lyophilized in containers such as vials, the vials may be stoppered, removed, and sealed.

The lyophilized carmustine composition in vials may be marketed as a pharmaceutical dosage form. The pharmaceutical dosage form of the present invention, although typically in vials, may be in any suitable containers, such as ampoules, syringes, co-vials, as long as they are capable of maintaining a sterile environment. Such containers may be made of glass or plastic, provided that the container material does not react with carmustine. The closure is typically a stopper, preferably a sterile rubber stopper, which affords a hermetic seal.

If carmustine is lyophilized in a large vessel, the lyophilized carmustine powder may be filled into containers, such as vials, after the completion of lyophilization. The lyophilized formulation of the present invention may be reconstituted with a sterile diluent, such as a dehydrated alcohol or another sterile liquid, to provide an appropriate solution of carmustine for administration. Alternatively, this solution is further diluted with water, saline, etc. to prepare a final dosing solution.

The present invention will now be described in details with examples.

A. Solubility

The solubility of carmustine in an alcoholic solvent, such as TBA and dehydrated ethanol, was performed and reported. The solubility of carmustine was visually determined by adding small aliquots of a solid sample of carmustine in 1 mL of a solvent at room temperature. The solubility of carmustine obtained is >1 g per mL in each of TBA and dehydrated ethanol at room temperature. Thus, in both TBA and dehydrated ethanol, carmustine is very soluble and the saturation limit is well above a working concentration. Neither of the solutions showed any sign of precipitation when the pre-lyophilized solution was stored at about 2 to about 8° C.

B. Stability

The stability of a carmustine solution in TBA or dehydrated ethanol was tested. The carmustine solution in either solvent was stable for at least 24 hrs upon storage at room temperature.

C. Lyophilization Cycle Development

Different pre-lyophilization formulations were prepared at various concentrations of carmustine in alcohols. Different lyophilization cycles were developed.

Based upon the information obtained from solubility and stability tests and information about ease of lyophilization, one preferred embodiment of the pre-lyophilization composition in accordance with the present invention has the following formulation:

| Ingredients | Concentration |
| --- | --- |
| Carmustine | About 3-400 mg/mL |
| Alcohol | About 10%-90% (v/v) |
| t-Butyl Alcohol q.s. to | Desired volume |

The alcohol in the above formulation may be selected from methanol, ethanol, dehydrated ethanol, n-propanol, or isopropanol.

The above pre-lyophilization compositions were prepared as follows: weighed a desired amount of carmustine and transferred it in to a suitable container; the carmustine was dissolved by adding a volume of a dehydrated alcohol and stirring for 15 minutes. After a clear yellow solution was obtained, diluted the solution to a desired volume with TBA and mixed well. Filtered the resulting solution through a 0.22μ filter and stored at 2-8° C. or at ambient temperature until filling into vials.

Another preferred embodiment of the pre-lyophilization composition has the following formulation:

| Ingredients | Concentration |
| --- | --- |
| Carmustine | About 3-400 mg/mL |
| Alcohol q.s. to | Desired volume |

The alcohol in the above formulation may be selected from methanol, ethanol, t-butanol, n-propanol, or isopropanol, and mixture thereof.

The above pre-lyophilization compositions were prepared as follows: weighed a desired amount of carmustine and transferred it in to a suitable container; the carmustine was dissolved by adding a desired volume of a dehydrated alcohol and stirring until well mixed. Filtered the resulting solution through a 0.22μ filter and stored at 2-8° C. or at ambient temperature until filling into vials.

A further preferred embodiment of the pre-lyophilization composition has the following formulation:

| Ingredients | Concentration |
| --- | --- |
| Carmustine | About 3-400 mg/mL |
| t-Butanol q.s. to | Desired volume |

The above pre-lyophilization compositions were prepared in the same manner as described for the compositions comprising carmustine and an alcohol, except that t-buantol may need to be warmed slightly to ensure it is in a liquid form. Yet the temperature of TBA and the solution should not be too high to cause degradation of carmustine. After a clear yellow solution was obtained, filtered it through a 0.22μ filter and stored at 2-8° C. or at ambient temperature until filling into vials.

D. Solvent Selection

To select a proper solvent ratio, TBA and ethanol were mixed in different ratios and observed for crystallization. 1 mL solution of two TBA:alcohol in a ratio of 98:2 and 95:5, respectively, was prepared, and the solution was placed at 20° C., 10° C., 8° C. and 2° C. for 2 hours at each temperature. Observed results are presented in a table form below:

|  | At 20° C. | At 10° C. | At 8° C. | At 2° C. |
| --- | --- | --- | --- | --- |
| TBA:Alcohol (98:2) | Solution | Solution | Solidified | Solidified |
| TBA:Alcohol (95:5) | Solution | Solution | Solution | Solidified | t-Butyl alcohol has a melting point slightly above 25° C. Thus it may be a clear liquid or a colorless solid, depending on the ambient temperature. It is very soluble in water and miscible with ethanol and diethyl ether. t-Butanol is useful for removal of water from substances. It is an authorized denaturant for ethanol. From the above table, it is noticeable that the freezing pointing of t-butanol (a slightly above 25° C.) is depressed by the addition of an alcohol.

Mixtures of TBA and alcohol and mixtures of TBA and water, with or without carmustine, were prepared and evaluated for their freezing points. 1 mL of each of the mixture was prepared and measured for its freezing temperature. Observed results are reported in a table below:

| Solvent mixture | Physical observation for freezing (° C.) |
| --- | --- |
| TBA:Alcohol (90:10) | −15 |
| TBA:Alcohol (94:6) + 100 mg Carmustine | 3 |
| TBA:Alcohol (95:5) + 100 mg Carmustine | 3 |
| TBA:Alcohol (98:2) + 100 mg Carmustine | 8 |
| TBA:Water (95:5) | −15 |

The above table shows that the addition of water or alcohol depresses the freezing point of TBA, but the addition of carmustine increase the freezing point of a TBA contained solvent mixture significantly, to above 0° C.

Example 1: Solubility and Solution Stability

The carmustine solubility test in TBA and other alcohols was performed in accordance with the procedure as described before.

For solution stability test, a drug solution was prepared in a solvent blend of alcohol:t-Butanol (10:90) at a carmustine concentration of 100 mg/mL, wherein the alcohol is ethanol. The drug solution was kept at room temperature in a closed stainless steel 316 vessel. The solution was studied for stability for up to 30 hours at 2 to 8° C. The solution showed acceptable stability over the course of study. Results from this study are shown in Table 1, which shows that the pre-lyophilization solution is very stable. At zero time point after preparation, it has an impurity level of RS A less than 0.1%. After storage at 2 to 8° C. for 30 hours, the impurity level of RS A is still less than 0.1%.

TABLE 1

Results from a solution hold time study

| Solution preparation | Sample hold time | Impurities RS A | Total Imp. |
|---|---|---|---|
| Carmustine in alcohol:TBA (10:90) | 0 hr | 0.02 | 0.10 |
| | 2 hr | 0.02 | 0.11 |
| | 4 hr | 0.03 | 0.12 |
| | 6 hr | 0.03 | 0.12 |
| | 8 hr | 0.02 | 0.12 |
| | 24 hr | 0.04 | 0.15 |
| | 30 hr | 0.04 | 0.15 |

Example 2: Formulation Optimization and Lyophilization Cycle Development

Example 2-A

A carmustine alcoholic solution was prepared in accordance with the procedure described before. The solution was frozen at a temperature between −40° C. to −20° C. and then dried under vacuum by evacuating the freeze-drying chamber to a pressure from about 250 mT to 50 mT at a primary drying at −30° C. to about 0° C. and a secondary drying to about 5° C. to about 20° C. In this process, the entire liquid sublimed and only empty vials were obtained at the end of the lyophilization cycle.

Example 2-B

A different drying approach than that in Example 2-A was used in this freeze-drying process. The primary drying was carried out at 5° C. higher temperature than that in Example 2-A under a vacuum pressure up to 500 mT. This process was also not successful. It produced empty vials or few vials with a thin film at the bottom of the vials.

Example 2-C

This freeze-drying process was similar to that in Example 2-B except that the pressure was set to a higher limit (about 900 mT). All other parameters were kept same as that in Example 2-A, namely, the freezing temperature was at about −40° C. to −20° C., a primary drying at −30° C. to about 0° C., and a secondary drying to about 5° C. to about 20° C. At the end of the lyophilization cycle, all the vials contained liquid droplets inside of the vials.

Example 2-D

A pre-lyophilization solution was prepared in alcoholic solvent and frozen. During the drying process, the frozen product was kept at −60° C. for 4 to 10 hrs and then warmed up to a temperature from about −55° C. to about −45° C. while pulling the vacuum of the chamber until dried mass was formed inside the vials (after 8 to 48 hours). The pre-lyophilized solution used in this lyophilization process was prepared in a single alcoholic solvent, such as methanol, ethanol, isopropyl alcohol, and n-butanol, and more preferably, a dehydrated alcohol thereof. When dehydrated ethanol was used, the process produced an acceptable, yet not ideal, dry mass on the bottom and sidewall of the glass vials.

Analytical results of the lyophilized carmustine formulations prepared in accordance with Example 2-D are presented in Table 2.

TABLE 2

Results of lyophilsates prepared from formulations using dehydrated ethanol.

| Trial | Sample | Impurities RS A | Total Imp. |
|---|---|---|---|
| 1 | Initial | 0.03 | 0.03 |

Initial: at the zero time after reconstitution

Table 2 shows that the carmustine lyophilsates prepared from pre-lyophilized formulations having a dehydrated alcohol only have an acceptable impurity profile. In Trial 2, only 0.03% of RS A was observed at time zero after reconstitution.

Example 2-E

In Example 2-E, the pre-lyophilization composition was prepared by using an alcoholic solvent mixture with TBA. The same lyophilization procedure in Example 2-D was used to lyophilize pre-lyophilization composition. However, the resulting lyophilisate did not dry completely and also melted at room temperature.

Example 2-F

In this lyophilization process, a carmustine solution is a mixture of anhydrous ethanol (also known as dehydrated alcohol) with TBA. The carmustine solution was frozen at a temperature lower than −40° C., more preferably −50° C. or lower. The frozen product was then dried at a primary drying temperature between about −45° C. to −30° C. and a secondary drying temperature between about −10° C. to 25° C. with a pressure of 900 mT Unexpectedly, this process yields lyophilized cakes with superior quality and uniformity in all vials.

Analytical test results of the lyophilsates from Example 2-F are presented in Table 3, Table 3 shows that the carmustine lyophilates prepared from pre-lyophilized formulations having a solvent mixture of a dehydrated alcohol (e.g., ethanol):TBA (10:90) showed excellent impurity profiles, even after one month storage at 25° C./60% RH. At zero time point after reconstitution, the lyophilized carmustine formulation has an impurity level of RS A less than 0.1%. After one month storage at 25° C./60% RH, the impurity level of RS A and the total impurity level are both less than 0.2%.

TABLE 3

Results of lyophilsates prepared from formulations using dehydrated alcohol:TBA (10:90)

| Trial | Sample | Impurities RS A | Total Imp. |
|---|---|---|---|
| 1 | Initial | NP | NP |
| | 1 M @25° C./60% RH | 0.05 | 0.09 |
| 2 | Initial | 0.03 | 0.03 |
| | 1 M @25° C./60% RH | 0.06 | 0.16 |

NP: Not Performed
Initial: at time zero
1 M: 1 month

In addition to the above examples, carmustine compositions were also prepared in pure t-butanol as the only solvent and freeze-dried. The temperature for freezing the carmustine compositions in 100% butanol (v/v) is lower than −30° C., and preferably lower than about −60° C. Then t-butanol was removed at a temperature higher than −30° C., preferably about 0° C., under vacuum. Optionally, the frozen solid may be further dried (i.e., further removal of butanol) using a secondary drying temperature from about 10° C. to 25° C.

Analytical test results are tabulated below in Table 4.

TABLE 4

Results of trials prepared by using TBA

| Trial | Sample | Impurities RS A | Total Imp. |
|---|---|---|---|
| 1 | Initial | 0.02 | 0.2 |

Example 3: Lyophilization Cycle

Weighed a desired amount of carmustine and transferred it to a container. This API was dissolved in a solvent with a pre-determined volume and stirred for 15 minutes. After a clear yellow solution was obtained, diluted the solution to a final volume with TBA and mixed well. The solvent may be about 5% to about 99% (v/v), more preferably about 5% to about 50% (v/v), even more preferably about 5% to about 15% (v/v) of a dehydrated alcohol, with the remaining percent being made up by TBA. Filtered this solution through a 0.22μ or lower filter and stored at 2 to 8° C. until filling it to vials. Frozen this solution to about −60° C. and held for about 2 hrs to 40 hrs. In one trial, evacuated the lyophilization chamber to a pressure of 900 Mt while warming up the shelves to about −55° C. Held the solid for 8 to 72 hrs, then further secondarily dried at about 20° C. for about 4 to 72 hrs. Additional trials were performed in accordance with the procedure described herein. In these trials, the pressures, temperatures used for primary drying and optionally for secondary drying were varied.

| Trial | Pressure (mT) | Parameter PD ° C. | SD ° C. | Sample | Impurities RS A | Total Imp. |
|---|---|---|---|---|---|---|
| 1 | 900 | −55 | 20 | Initial | 0.07 | 0.07 |
|   |     |     |    | 1 M @ 25° C./60% RH | 0.05 | 0.10 |
| 2 | 900 | −40 | 15 | Initial | 0.05 | 0.05 |
|   |     |     |    | 1 M @ 25° C./60% RH | 0.04 | 0.09 |
| 3 | 900 | −50 | 15 | Initial | 0.01 | 0.01 |
|   |     |     |    | 1 M @ 25° C./60% RH | 0.06 | 0.08 |
| 4 | 900 | −50 | 25 | Initial | 0.01 | 0.01 |
|   |     |     |    | 1 M @ 25° C./60% RH | 0.07 | 0.11 |
| 5 | 900 | −50 | 20 | Initial | 0.04 | 0.08 |
|   |     |     |    | 1 M @ 25° C./60% RH | 0.07 | 0.10 |
| 6 | 900 | −40 | 20 | Initial | 0.04 | 0.06 |
|   |     |     |    | 1 M @ 25° C./60% RH | 0.04 | 0.15 |
| 7 | 900 | −45 | 20 | Initial | 0.04 | 0.07 |
|   |     |     |    | 1 M @ 25° C./60% RH | 0.05 | 0.16 |
| 8 | 750 | −45 | 10 | Initial | 0.05 | 0.08 |
| 9 | 900 | −45 | 0  | Initial | 0.05 | 0.09 |
| 10 | 750 | −50 | 20 | Initial | 0.03 | 0.07 |
|    |     |     |    | 1 M @ 25° C./60% RH | 0.08 | 0.12 |
| 11 | 150 | −32 | 20 | Initial | 0.01 | 0.04 |
|    |     |     |    | 1 M @ 25° C./60% RH | 0.01 | 0.05 |
| 12 | 150 | −34 | 22 | Initial | 0.01 | 0.02 |
|    |     |     |    | 1 M @ 25° C./60% RH | 0.01 | 0.05 |
| 13 | 100 | −36 | 20 | Initial | 0.03 | 0.05 |
|    |     |     |    | 1 M @ 25° C./60% RH | 0.13 | 0.15 |

PD: Primary drying
SD: Secondary drying
Initial: at time zero
1 M: 1 month

Table 5 shows that in the lyophilization process as described in Example 3, wherein the primary drying temperature was between −55 to −32° C., and optionally the secondary drying temperature was between 0 to 25° C., the resulting lyophilized carmustine formulations have excellent impurity profiles.

It should be noted that the invention in its broader aspects is not limited to the specific details, representative compositions, methods, and processes, and illustrative examples described in connection with the preferred embodiments and preferred methods. Modifications and equivalents will be apparent to practitioners skilled in this art and are encompassed within the spirit and scope of the appended claims.

What is claimed is:

1. A pharmaceutical formulation for lyophilization consisting essentially of
    about 3 mg/mL to about 400 mg/mL carmustine and
    a dehydrated solvent system consisting of t-butanol and about 5% to about 25% of one or more alcohols selected from ethanol and isopropanol.

2. The pharmaceutical formulation for lyophilization of claim 1, wherein the carmustine is present at a concentration of about 10 mg/mL to about 200 mg/mL.

3. The pharmaceutical formulation for lyophilization of claim 2, wherein the carmustine is present at a concentration of about 50 mg/mL to 100 mg/mL.

4. The pharmaceutical formulation of claim 1, wherein the one or more alcohols is dehydrated ethyl alcohol.

5. The pharmaceutical formulation of claim 1, wherein t-butanol and the dehydrated alcohol is in a ratio of 90:10 (v/v).

6. The pharmaceutical formulation of claim 1, wherein the one or more alcohols is a dehydrated isopropyl alcohol.

7. The pharmaceutical formulation of claim 1, wherein t-butanol and the dehydrated alcohol is in a ratio of 95:5 (v/v).

8. The pharmaceutical formulation according to claim 5, wherein said pharmaceutical composition contains not more than about 0.1% of 1,3-bis(2-chloroethyl)urea after storage at 2 to 8° C. for 36 hours.

* * * * *